(12) United States Patent
Chung

(10) Patent No.: US 9,795,336 B2
(45) Date of Patent: Oct. 24, 2017

(54) DEVICE FOR MEASURING URINARY DETRUSOR PRESSURE

(71) Applicants: GACHON UNIVERSITY OF INDUSTRY-ACADEMIC COOPERATION FOUNDATION, Gyeonggi-do (KR); GIL MEDICAL CENTER, Incheon (KR)

(72) Inventor: Kyung Jin Chung, Seoul (KR)

(73) Assignees: GACHON UNIVERSITY OF INDUSTRY-ACADEMIC COOPERATION FOUNDATION, Gyeonggi-Do (KR); GIL MEDICAL CENTER, Incheon (KR)

( * ) Notice: Subject to any disclaimer, the term of this patent is extended or adjusted under 35 U.S.C. 154(b) by 53 days.

(21) Appl. No.: 14/411,603

(22) PCT Filed: Apr. 18, 2014

(86) PCT No.: PCT/KR2014/003386
§ 371 (c)(1),
(2) Date: Dec. 29, 2014

(87) PCT Pub. No.: WO2014/175601
PCT Pub. Date: Oct. 30, 2014

(65) Prior Publication Data
US 2016/0058355 A1   Mar. 3, 2016

(30) Foreign Application Priority Data
Apr. 23, 2013 (KR) ......................... 10-2013-0045039

(51) Int. Cl.
*A61B 5/00* (2006.01)
*A61B 5/20* (2006.01)
(Continued)

(52) U.S. Cl.
CPC .......... *A61B 5/205* (2013.01); *A61B 5/04882* (2013.01); *A61B 5/04884* (2013.01);
(Continued)

(58) Field of Classification Search
CPC ....................................... A61B 5/205
See application file for complete search history.

(56) References Cited

U.S. PATENT DOCUMENTS 4,612,939 A * 9/1986 Robertson .............. A61B 5/205
                                                           600/135
5,167,237 A * 12/1992 Rabin .................... A61B 5/205
                                                           128/836
(Continued)

FOREIGN PATENT DOCUMENTS

CN   102325493   1/2012
CN   102631191   8/2012
(Continued)

OTHER PUBLICATIONS

First Office Action Issued by the State Intellectual Property Office of PRC for Appln. No. 2014-80001713.8 Dated March 17, 2016.
International Search Report for PCT/KR2014/003386.

*Primary Examiner* — John R Downey
(74) *Attorney, Agent, or Firm* — Gottlieb, Rackman & Reisman, P.C.

(57) ABSTRACT

The present invention relates to a device for measuring bladder pressure, comprising: a measurement rod inserted into the abdomen of a user to measure both abdomen pressure and bladder pressure; and a body unit provided to be worn on the waist of the user and electrically connected to the measurement rod so as to calculate and store urinary detrusor pressure measured by subtracting a measurement abdomen pressure from a measurement bladder pressure measured by the measurement rod.

15 Claims, 6 Drawing Sheets

(51) Int. Cl.
*A61B 5/0488* (2006.01)
*A61B 17/34* (2006.01)
*A61B 17/00* (2006.01)

(52) U.S. Cl.
CPC .......... *A61B 5/6823* (2013.01); *A61B 5/6831* (2013.01); *A61B 5/6848* (2013.01); *A61B 5/7278* (2013.01); *A61B 5/742* (2013.01); *A61B 5/7475* (2013.01); *A61B 17/3415* (2013.01); *A61B 2017/00004* (2013.01)

(56) References Cited

U.S. PATENT DOCUMENTS

| | | | | |
|---|---|---|---|---|
| 2002/0115906 | A1* | 8/2002 | Miller | A61M 13/003 600/31 |
| 2003/0204149 | A1* | 10/2003 | Streng | A61B 5/04882 600/546 |
| 2010/0240967 | A1* | 9/2010 | Kim | A61B 5/02055 600/301 |

FOREIGN PATENT DOCUMENTS

| | | |
|---|---|---|
| KR | 10-20030090171 | 11/2003 |
| KR | 10-2006-00 I9397 | 3/2006 |
| KR | 100689097 | 3/2007 |
| KR | 100984807 | 10/2010 |

\* cited by examiner

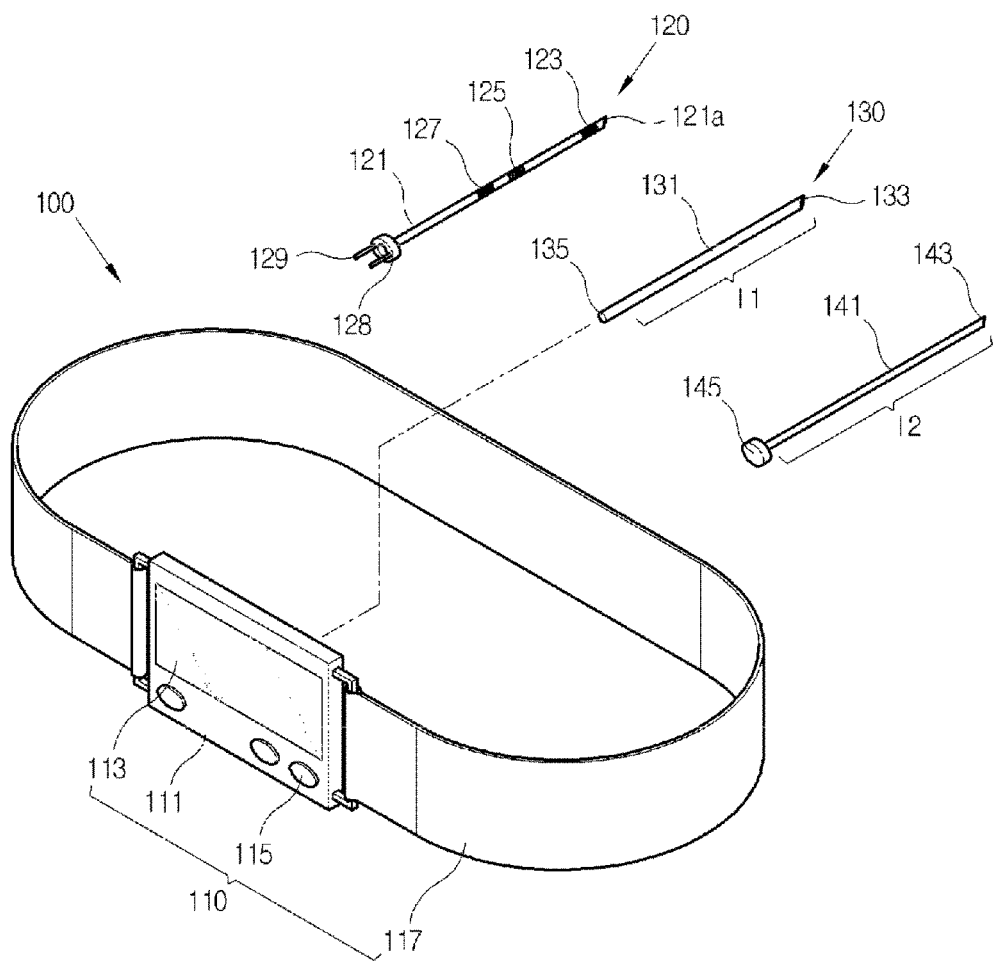
[Fig. 1]

[Fig. 2]
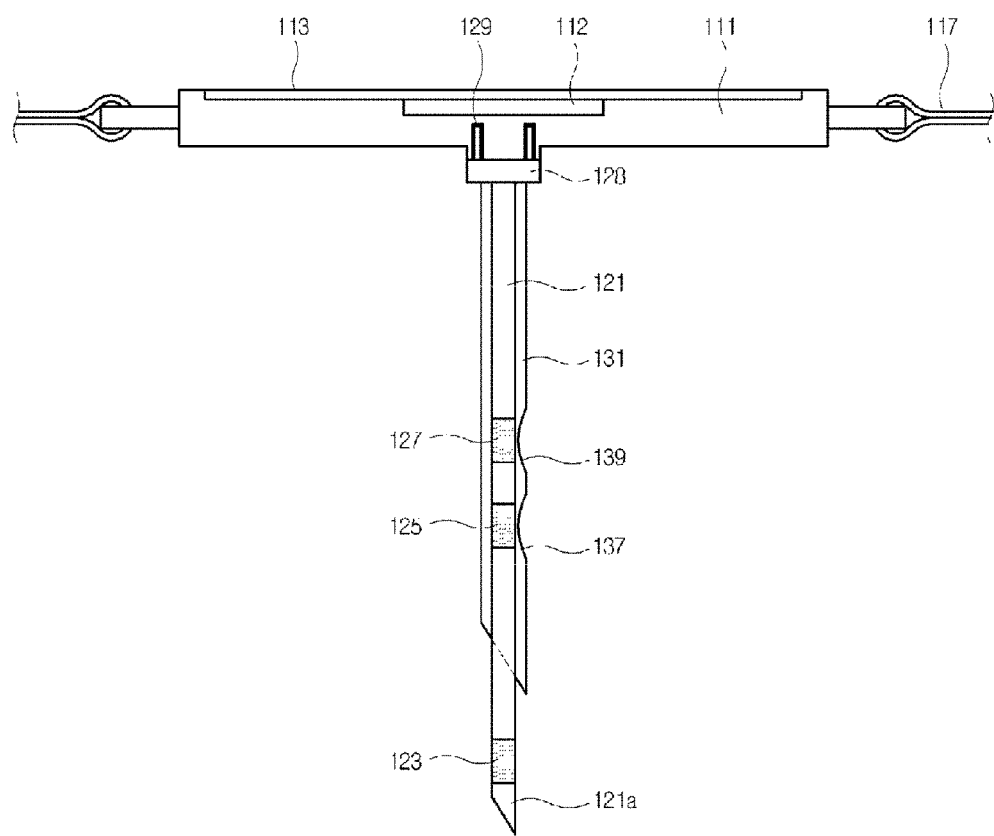

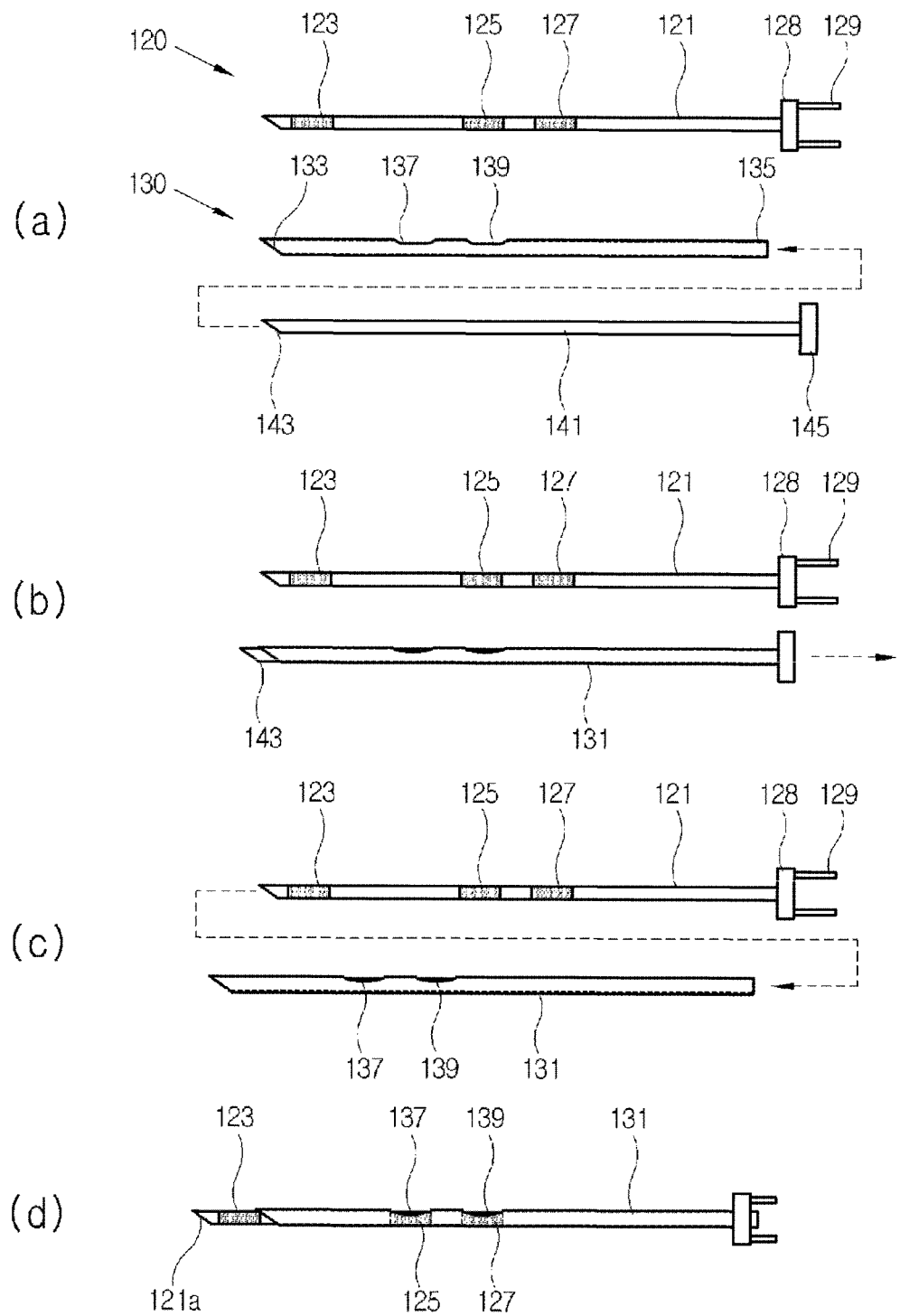
[Fig. 3]

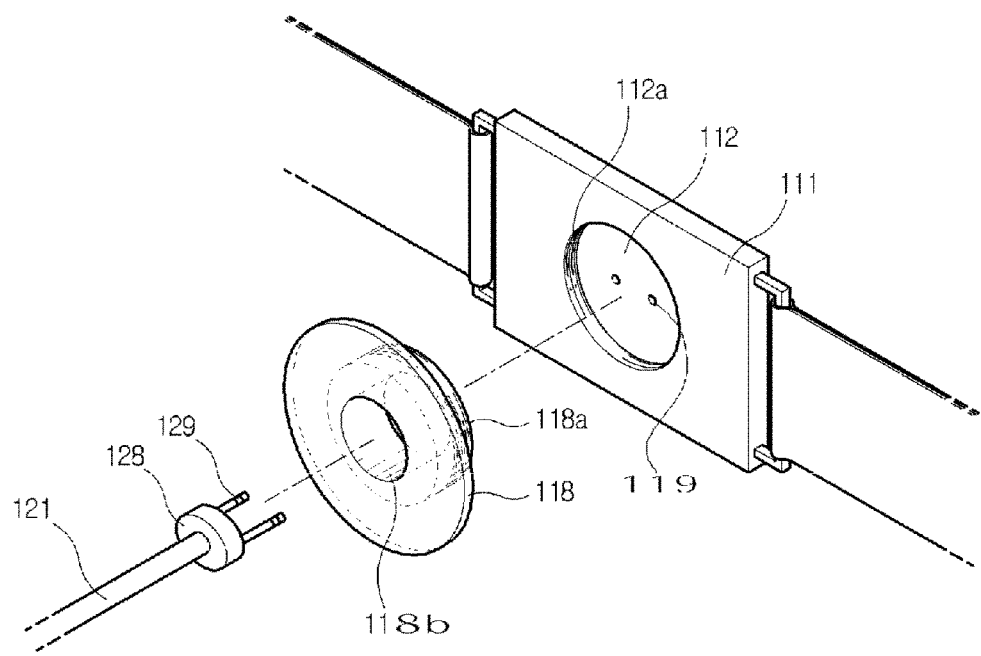
[Fig. 4]

[Fig. 5]
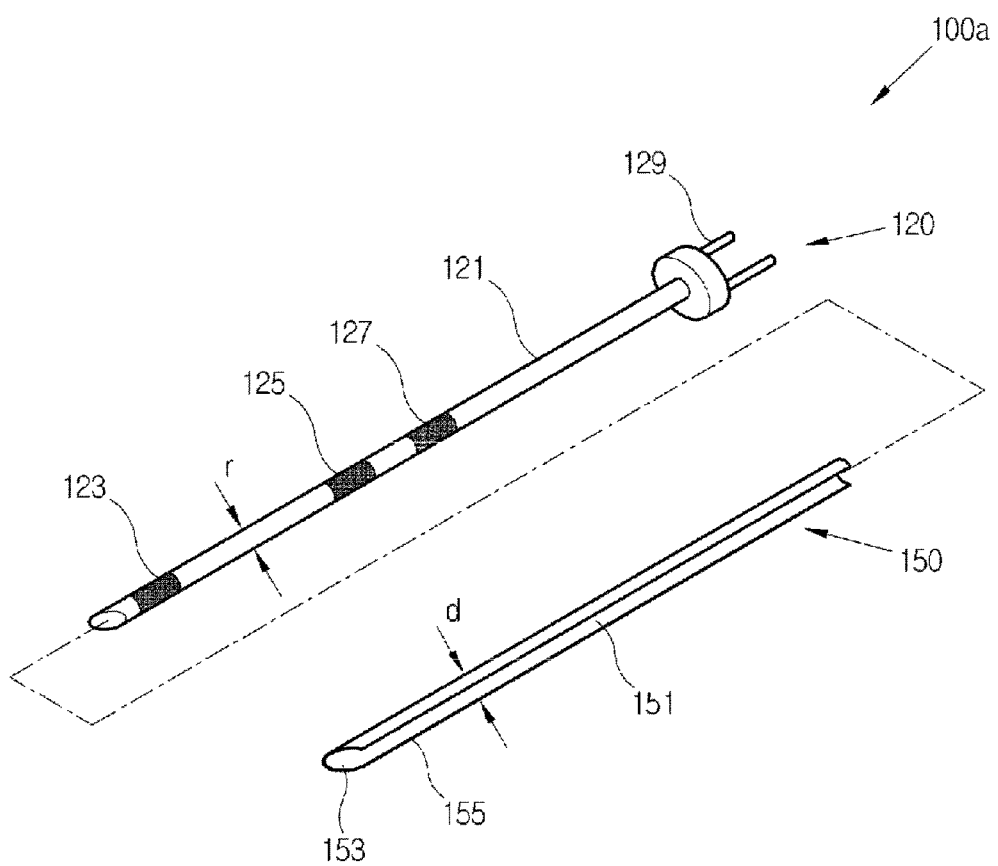

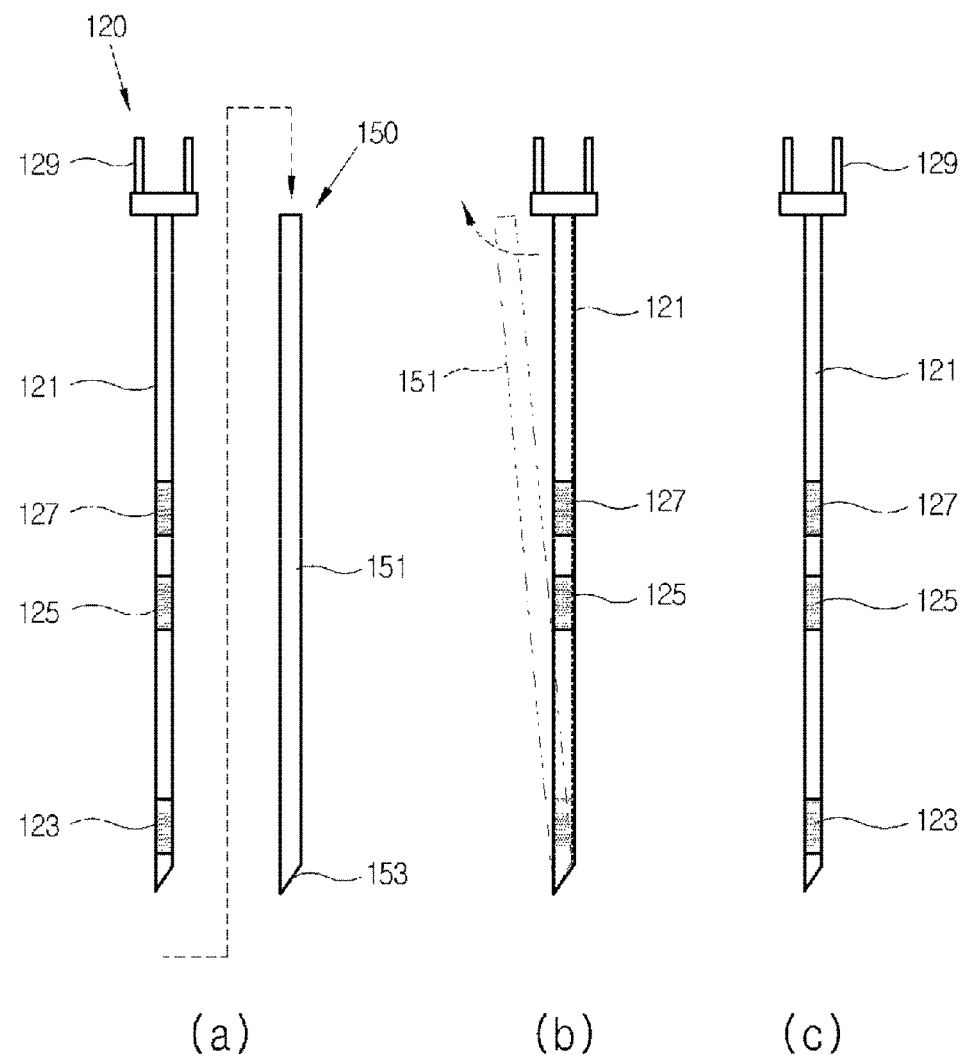
[Fig. 6]

DEVICE FOR MEASURING URINARY DETRUSOR PRESSURE

This application is the U.S. National Stage Application of PCT/KR2014/003386 filed Apr. 18, 2014, which claims priority from Korean Application No. 10-2013-0045039 filed Apr. 23, 2013.

TECHNICAL FIELD

The present invention relates to a device for measuring bladder pressure, and more particularly, to a device for measuring bladder pressure, which can measure both bladder pressure and abdominal pressure, thereby calculating accurate detrusor pressure.

BACKGROUND ART

The measurement of bladder pressure is a basic test in urodynamic examinations, and is a method of investigating bladder functionality regarding a bladder volume, capacity and contractility, detrusor contractility, and drug reactions while recording changes in pressure occurring during bladder filling and urination.

Bladder pressure is examined using bladder pressure measurement equipment. However, since bladder pressure is a pressure that appears during urination, it is the sum of abdominal pressure and detrusor pressure. Accordingly, abdominal pressure should be subtracted from bladder pressure in order to calculate detrusor pressure actually indicative of bladder functionality. For this reason, conventional bladder pressure measurement equipment includes a bladder pressure measurement catheter configured to be inserted into the urethra in order to measure detrusor pressure, an abdominal pressure measurement balloon configured to be inserted into the anus or the vagina in the case of a female patient in order to measure abdominal pressure, and an electromyography unit configured to examine the organic motion of sphincters.

Therefore, to measure detrusor pressure, a patient's genitalia must be exposed, and in this state, the bladder pressure measurement catheter must be inserted through the urethra, and the abdominal pressure measurement balloon must be inserted through the vagina or anus. In addition, while physiological saline is artificially injected directly into the bladder of the subject at a position close to an urodynamic device, changes in intravesical pressure and the pattern of urination are examined while the subject delays urination for a specific time or urinates according to the examiner's instructions.

This conventional system for measuring bladder pressure has several disadvantages. First, it can cause significant embarrassment not only to a subject but also to an examiner. Specifically, the urethral, genital and anal sites are necessarily exposed during the preparation of examination, and the examiner must touch the exposed site or insert the device into the site, and the subject must urinate next to the examination device according to the examiner's instructions, and for these reasons, the subject is likely to feel great embarrassment. Additionally, the examiner who performs this procedure can feel psychological discomfort. In addition, due to the repeated insertion of the catheter into the urethra during examination, the subject can experience side effects, including urinary tract infection, haematuria, and painful urination.

Furthermore, since urine flows down along the outside of the catheter, the examination place is apt to be contaminated with urine. In addition, the measurement device has a problem in terms of accuracy. Specifically, since the catheter is inserted into the urethra, which is the outlet for urine, the catheter itself impedes urination to interfere with accurate examination. Also, since examination is performed while the bladder is artificially filled with physiological saline within a short time due to the temporal and spatial limitations of examination, natural physiological urination cannot be reproduced. In addition, since the subject urinates near the examiner according to the examiner's instructions, the resulting embarrassment can also impede actual urination. In various respects as described above, it is difficult to trust the accuracy of conventional examination.

In this regard, Korean Patent Application Publication No. 10-2009-0082636 entitled "Method for Measuring Abdominal Pressure using Surface Electromyography" and Korean Patent Application Publication No. 10-2003-0090171 entitled "Portable Device for Monitoring Intravesical Pressure and Bladder Neck Pressure" disclose relevant contents. However, the technologies disclosed in such patent documents measure abdominal pressure electromyographically or separately measure only bladder pressure, and are thus problematic in that they cannot measure both abdominal pressure and bladder pressure.

DISCLOSURE

Technical Problem

The present invention has been made in order to solve the above-described problems, and an object of the present invention is to provide a device for measuring bladder pressure, which can measure both bladder pressure and abdominal pressure and determine actual detrusor pressure, exclusive of the abdominal pressure.

Another object of the present invention is to provide a device for measuring bladder pressure, which has a simple configuration and can measure bladder pressure in a convenient and accurate manner in a situation similar to actual urination without causing embarrassment to both an examiner and a subject.

The above objects and various advantages of the present invention will be more clearly understood by those skilled in the art from preferred embodiments of the present invention.

Technical Solution

The objects of the present invention can be achieved by the following device for measuring bladder pressure. A device for measuring bladder pressure according to the present invention includes a measurement rod configured to be inserted into the abdomen of a user, to measure both abdominal pressure and bladder pressure; and a body unit configured to be worn on the waist of the user, to be electrically connected with the measurement rod, to calculate and store detrusor pressure obtained by subtracting the measured abdominal pressure from the bladder pressure measured by the measurement rod.

According to an embodiment of the present invention, the device for measuring bladder pressure further includes a guide tube configured to penetrate and be inserted into the abdomen of the user, and receive the measurement rod within it, to guide the measurement rod.

According to an embodiment of the present invention, the body unit includes a body having a display unit and an input unit; an adapter provided on the backside of the body to come into contact with the abdomen of the user, and to be electrically connected with the measurement rod; and a belt coupled to both sides of the body, and configured to be worn on the waist of the user.

According to an embodiment of the present invention, the device includes a wireless control unit configured to be separate from the body unit, to enable an inputting person to input signals using buttons.

According to an embodiment of the present invention, the measurement rod includes a rod body having a predetermined length; a bladder pressure measurement unit configured to be provided at the lower end of the rod body, to measure the bladder pressure of the user; an abdominal pressure measurement unit configured to be spaced apart from the bladder pressure measurement unit, to measure the abdominal pressure of the user; and a connector configured to be provided at the upper end of the rod unit, and to be connected to the adapter.

According to an embodiment of the present invention, the body further includes a length control bracket configured to be screw-coupled with the backside of the body, to control the depth of insertion of the measurement rod; wherein a position within the abdomen, into which the abdominal pressure measurement unit is inserted, is controlled by controlling the screw coupling length between the length control bracket and the body.

According to an embodiment of the present invention, the guide tube is formed of a metal material, and is configured such that a sharp needle is formed at a lower end of the guide tube and a discharge slit from which the measurement rod can be separated is formed along an axial direction of the guide tube to have a diameter larger than that of the measurement rod.

According to an embodiment of the present invention, the guide tube is formed of a polymer material or a metal material.

According to an embodiment of the present invention, the guide tube is formed of a biodegradable polymer material that is degraded by body fluids.

According to an embodiment of the present invention, the device further includes a penetrating needle configured to be inserted into the guide tube, penetrate the abdomen of the user through the guidance of the guide tube, and then form an insertion hole through which the measurement rod is inserted when the guide tube is formed of a biodegradable polymer material.

According to an embodiment of the present invention, the penetrating needle is separated from the guide tube after its penetration into the abdomen of the user, and then the measurement rod is inserted into the abdomen through the guide tube.

According to an embodiment of the present invention, a measurement unit exposing hole having a predetermined size is formed penetrating through the outer circumferential surface of the guide tube at a position corresponding to the position of the abdominal pressure measurement unit.

According to an embodiment of the present invention, the abdominal pressure measurement unit includes a plurality of abdominal pressure measurement units spaced apart from each other.

According to an embodiment of the present invention, the device further includes a sphincter electromyography unit configured to be attached to the sphincter side of the user, and to measure sphincter electromyographic activity; wherein the body unit determines whether the organic motion of detrusor and sphincter muscles is normal based on the measured sphincter electromyographic activity.

Advantageous Effects

The device for measuring bladder pressure according to the present invention can simultaneously measure bladder pressure, abdominal pressure and sphincter electromyographic activity in the state in which the measurement rod has been inserted in the abdomen of a user, thereby accurately measuring actual detrusor pressure, exclusive of abdominal pressure, and sphincter electromyographic activity.

In addition, an insertion hole can be easily formed in the abdomen by using the guide tube and the penetrating needle, and then the measurement rod can be inserted therein. Furthermore, the body unit is securely fastened to the abdomen of the user in the form of a belt or a patch. Accordingly, a user can measure bladder pressure in a convenient and accurate manner.

DESCRIPTION OF DRAWINGS

FIG. 1 is a perspective view illustrating the configuration of a device for measuring bladder pressure according to the present invention;

FIG. 2 is a schematic view illustrating the combined state of a device for measuring bladder pressure according to the present invention;

FIG. 3 is a view illustrating a process of using a device for measuring bladder pressure according to the present invention;

FIG. 4 is a view illustrating a process of combining a measurement rod with the body unit of a device for measuring bladder pressure according to the present invention;

FIG. 5 is a perspective view illustrating the configuration of a device for measuring bladder pressure according to another embodiment of the present invention; and FIG. 6 is a view illustrating a process of using a device for measuring bladder pressure according to another embodiment of the present invention.

DESCRIPTION OF REFERENCE NUMERALS

100: device for measuring bladder pressure
110: body unit 111: body 113: display unit
115: input unit 116: storage unit 117: belt
119: adapter 120: measurement rod
121: rod body 123: bladder pressure measurement unit
125: first abdominal pressure measurement unit
127: second abdominal pressure measurement unit
128: connector support 129: connector
130: guide tube 131: guide tube body
133: lower opening 135: upper opening
137: first measurement unit exposing hole
139: second measurement unit exposing hole
140: penetrating needle 141: needle body
143: needle 145: support rod 150: guide needle
151: guide needle body 155: discharge slit.

MODE FOR INVENTION

Preferred embodiments of the present invention will be described with reference to the accompanying drawings below in order to provide a better understanding of the present invention. The embodiments of the present invention can be implemented in various forms, and should not be interpreted as being limited to the embodiments described in detail below. These embodiments are provided such that this disclosure will be thorough and complete and will fully convey the concept of the invention to those skilled in the art. Accordingly, the shape and the like of elements in the drawings may be exaggerated in order to clearly illustrate features of the embodiments. In the drawings, like components are denoted by like reference numerals. In the following description, the detailed description of known functions and configurations incorporated herein will be omitted when it may obscure the subject matter of the present invention.

FIG. 1 is a perspective view illustrating the configuration of a bladder pressure measurement device 100 according to the present invention, and FIG. 2 is a view illustrating the assembled state of the bladder pressure measurement device 100.

As shown in the drawings, the bladder pressure measurement device 100 according to the present invention includes a body unit 110 configured to be worn on the waist of a user, a measurement rod 120 configured to be inserted into the abdomen of the user and to measure abdominal pressure and bladder pressure, a guide tube 130 configured to guide the insertion of the measurement rod 120 into the abdomen, and a penetrating needle 140 configured to form an insertion hole in the abdomen and allow the measurement rod 120 to be inserted into the abdomen. In addition, although not shown in the drawings, the bladder pressure measurement device 100 includes a sphincter electromyography unit (not shown) that is attached to the skin neighboring sphincters and measures the electromyographic activity of sphincters.

The body unit 110 is connected with the measurement rod 120, and calculates actual detrusor pressure based on the measured bladder pressure and abdominal pressure. The body unit 110 includes a body 111 disposed on the abdomen; a display unit 113 configured to be provided on the front side of the body 111 to display the measured bladder pressure and abdominal pressure, the measured electromyographic activity and the calculated detrusor pressure; an input unit 115 configured to receive an input signal from the user; a storage unit 116 configured to provided in the body 111 and store the measured bladder pressure and abdominal pressure, the measured electromyographic activity and the calculated detrusor pressure; a belt 117 or patch configured to fasten the body 111 to the abdomen of the user; an adapter 119 electrically connected with the measurement rod 120; and a length control bracket 118 configured to control the depth of insertion of the measurement rod 120 into the abdomen.

In this case, the body unit 110 may be operated by applying power through a power supply line (not shown), or may include a battery (not shown) for supplying power.

The body 111 is formed in a hull shape having a specific size. The body 111 is formed of a durable material so that it can be repeatedly used over a long period of time. The body 111 includes a display unit 113, an input unit 115, a storage unit 116, an adapter 119, a control unit (not shown) configured to control the measurement rod 120, and a connection (not shown) with a computer mainframe that can be connected separately.

The display unit 113 displays the bladder pressure and abdominal pressure measured by the measurement rod 120, the sphincter electromyographic activity measured by a sphincter electromyography unit (not shown), and the detrusor pressure calculated by a control unit (not shown). This enables a user or a doctor to easily become aware of the current bladder pressure of the user.

The input unit 115 receives an input signal associated with the driving of the body unit 110 and the measurement rod 120. The input unit 115 may be embodied in the form of a plurality of buttons integrated with the body unit 110, and may include a separate wireless control unit (not shown), such as a remote control, so as to enable an inputting person to conveniently input signals.

In this case, the inputting person may be a subject, a doctor, or a nurse.

The input unit 115 and the wireless control unit (not shown) may include a power button, a reset button configured to restore factory default settings, a history button configured to allow bladder pressure particulars, stored in the storage unit 116, to be displayed on the display unit 113, etc.

In the storage unit 116, the measured bladder pressure and abdominal pressure, the measured electromyographic activity and the calculated detrusor pressure are stored on a per-time period basis. The user can view information, stored in the storage unit 116, via the display unit 113 or the monitor of a separately connected computer mainframe.

The belt 117 or the patch allows the user to fasten the body 111 to the abdomen in order to measure bladder pressure. Through the belt 117 or the patch, the body 111 is securely fastened to the abdomen of the user, and in this state, is connected to the measurement rod 120. The belt 117 may be provided in the form of an elastic ring, as shown in the drawings, may be provided so that both ends are coupled to each other by a fastening member (not shown), or may be attached to the abdomen in a patch form.

As shown in FIG. 4, the adapter 119 is provided on the backside of the body 111. The adaptor 119 is electrically connected with the connector 129 of the measurement rod 120 inserted into the abdomen so that the bladder pressure and abdominal pressure measured by the measurement rod 120 are transferred to a control unit (not shown).

The length control bracket 118 is provided such that the connector 129 is inserted therein and passed therethrough, and is coupled to the backside of the body 111. The connector 129 is inserted therein and electrically connected to the adapter 119 that is provided on the backside of the body 111.

Depending on the depth to which the length control bracket 118 is inserted into the insertion groove 112 of the body 111, the depth to which the abdominal pressure measurement units 125 and 127 of the measurement rod 120 are inserted into the abdomen, that is, the abdominal pressure measurement position, is controlled.

On the inner circumferential surface of the insertion groove 112 and the outer circumferential surface of the length control bracket 118, male and female screw threads 112a and 118a are formed, respectively. Accordingly, depending on the screw coupling length between the insertion groove 112 and the length control bracket 118, the length by which the measurement rod 120 is inserted into the abdomen of the user can be controlled.

The measurement rod 120 is inserted into the abdomen of the user, and measures bladder pressure and abdominal pressure occurring during bladder filling and urination. The measurement rod 120 includes a rod body 121; a bladder pressure measurement unit 123 configured to be provided at the lower end of the rod body 121 to measure bladder pressure; a first abdominal pressure measurement unit 125 provided to be spaced apart from the bladder pressure measurement unit 123 by a specific distance to measure abdominal pressure; a second abdominal pressure measurement unit 127 provided to be spaced apart from the first abdominal pressure measurement unit 125 to measure abdominal pressure; a connector 129 electrically connected to the body unit 110; and a connector support 128 configured to support the connector 129.

The rod body 121 is formed in a rod shape having a specific length, and is formed to have elasticity so that it will not damage the inner wall of the bladder. The rod body 121 is inserted into the abdomen of the user in the state in which it is received in a guide tube 130. The rod body 121 is formed to be longer than the guide tube 130 so that the lower end 121a and the bladder pressure measurement unit 123 can be exposed from the lower end of the guide tube 130.

The bladder pressure measurement unit 123 is provided at the lower end of the rod body 121, and measures bladder pressure. The bladder pressure measurement unit 123 is provided at a position that allows the bladder pressure measurement unit 123 to come into contact with the bladder, and measures changes in bladder pressure during bladder filling and urination. The bladder pressure measurement unit 123 is provided in the form of a pressure sensor, and bladder pressure measured by the bladder pressure measurement unit 123 is transferred to the body 111 through the connector 129.

The first abdominal pressure measure unit 125 and the second abdominal pressure measure unit 127 are disposed to be spaced apart from each other, and measures abdominal pressure. The first abdominal pressure measure unit 125 and the second abdominal pressure measure unit 127 are provided on the rod body 121 to come into contact with the abdomen of the user. Using these units, abdominal pressure that is applied to the abdomen during bladder filling and urination is measured. The first abdominal pressure measure unit 125 and the second abdominal pressure measure unit 127 are provided in the form of a pressure sensor, and abdominal pressures measured thereby are transferred to the body 111.

The abdominal pressure measure unit 125 and the second abdominal pressure measure unit 127 may simultaneously measure pressures occurring in different abdominal layers, thereby determining the depth of insertion of the measurement rod, or may be used alternately to measure pressure, thereby increasing the accuracy of measurement. The use of each of the abdominal pressure measure unit 125 and the second abdominal pressure measure unit 127 may be set by a user via the input unit 115, or can be automatically determined through comparison with the pressure measured by the bladder pressure measurement unit 123. This can be used to determine an abdominal pressure measurement unit that measures abdominal pressure through automatic comparison with the pressure measured by the bladder pressure measurement unit 123 when the depth of a site to be measured for abdominal pressure is changed by urination or a change in abdominal pressure.

The connector support 128 is provided at the upper end of the rod body 121 and support the connector 129 and the rod body 121. The connector support 128 is formed to have a diameter larger than that of the rod body 121. Accordingly, even when the measurement rod 120 is inserted into the guide tube 130, the connector support 128 limits the length of insertion of the rod body 121 in the state in which it has been placed at the upper end of the guide tube 130.

As shown in FIG. 4, the connector 129 is inserted into the adapter 119 of the body 111. In this case, the bladder pressure measurement device 100 according to a preferred embodiment of the present invention is configured such that the connector 129 is provided in the form of a rod having a specific length, and the adapter 119 is provided in the form of an insertion groove into which the rod is to be inserted. However, on the contrary, in some cases, the connector may be provided in the form of an insertion groove, and the adapter 119 may be provided in the form of a rod.

The guide tube 130 guides the penetrating needle 140 through the penetration of into the abdomen of the user, and guides the measurement rod 120 through the insertion of into the abdomen of the user after the removal of the penetrating needle 140.

The guide tube 130 includes a hollow-shaped guide tube body 131 open at the upper and lower ends; and measurement unit exposing holes 137 and 139 formed through the guide tube body 131 in the axial direction of the guide tube body 131 at positions corresponding to the positions of the abdominal pressure measurement units 125 and 127.

The guide tube 130 is formed to have an inner diameter larger than the outer diameter of the penetrating needle 140 and the outer diameter of the rod body 121. Accordingly, the penetrating needle 140 and the rod body 121 can be easily inserted into the guide tube 130. The guide tube 130 may be formed of a polymer material or a biodegradable material.

As shown in FIG. 2, the first measurement unit exposing hole 137 and the second measurement unit exposing hole 139 allow the first abdominal pressure measurement unit 125 and the second abdominal pressure measurement unit 127 to be exposed to the outside of the guide tube 130 when the measurement rod 120 is received in the guide tube 130. Alternatively, when the guide tube 130 is formed of a biodegradable material, it will be easily degraded by body fluids even in the absence of the measurement unit exposing units, and thus will be degraded within a short time after its insertion into the abdomen. Accordingly, the first abdominal pressure measurement unit 125 and the second abdominal pressure measurement unit 127 can measure abdominal pressure while in direct contact with the abdominal wall.

The penetrating needle 140 penetrates the abdomen of the user in combination with the guide tube 130 and forms an insertion hole (not shown) having a specific size, into which the measurement rod 120 is to be inserted. The penetrating needle 140 includes a needle body 141 formed of a rigid metal material; a needle 143 configured to be formed sharply at the lower end of the needle body 141 and penetrate the abdomen; and a support rod 145 configured to serve as a handle and limit the depth of insertion of the penetrating needle 140.

The needle body 141 is formed of a metal material. The penetrating needle 140 penetrates the abdomen under pressure, applied to the abdomen of the user, in the state in which it has been inserted into the guide tube 130. The penetrating needle 140 is separated from the guide tube 130 after it has formed an insertion hole (not shown) in the abdomen.

A process of using the bladder pressure measurement device 100 according to the present invention, which has the above-described configuration, is now described with reference to FIGS. 1 to 4.

As shown in FIG. 3(a), a user prepares the measurement rod 120, the guide tube 130, and the penetrating needle 140. Then, as shown in FIG. 3(b), the penetrating needle 140 is inserted into the guide tube 130. At this time, the needle 143 of the penetrating needle 140 is exposed from the lower end of the guide tube 130 because the length 12 of the penetrating needle 140 is longer than the length 11 of the guide tube 130.

The guide tube 130 including the penetrating needle 140 received therein is gripped by the user's hand and pressed against the abdomen. Then, the needle 143 penetrates the abdomen, and the penetrating needle 140 and the guide tube 130 are inserted into the abdomen.

In this state in which the guide tube 130 and the penetrating needle 140 have been inserted into the abdomen, the penetrating needle 140 is separated from the guide tube 130 by the user's hand.

Then, as shown in FIG. 3(c), the measurement rod 120 is inserted into the guide tube 130 inserted into the abdomen. The lower end of the measurement rod 120 is inserted into the abdomen to a specific depth through an insertion hole (not shown), and is inserted into the bladder. In the state in which the measurement rod 120 has been inserted into the guide tube 130 as shown in FIG. 3(d), a user wears the body unit 110 on his or her waist, connects the connector 129 to the adapter 119 as shown in FIG. 4, controls the appropriate depth of insertion of the measurement rod 120 by controlling the screw coupling length of the length control bracket 118 while checking pressure, and then fastens the body unit to the abdomen using the belt 117 or a patch (not shown).

Meanwhile, a sphincter electromyography unit (not shown) is attached to the skin neighboring the sphincter of the user. The sphincter electromyography unit (not shown) is provided as a patch-type electrical sensor.

When power is applied, the bladder pressure measurement unit 123 measures bladder pressure, and the first abdominal pressure measurement unit 125 and the second abdominal pressure measurement unit 127 measure abdominal pressure. A sphincter electromyography unit (not shown) measures sphincter electromyographic activity. The measured bladder pressure, abdominal pressure and electromyographic activity are transferred to the body unit 110, and a control unit (not shown) calculates detrusor pressure by subtracting the measured abdominal pressure from the measured bladder pressure. The determined detrusor pressure is stored in the body unit 110 on a per-time period basis, and the stored information can be viewed via a separately connected computer mainframe (not shown).

The measurement rod 120 is securely fastened to the body unit 110 in the state in which it has been inserted in the abdomen along with the guide tube 130, and the body unit 110 is fastened to the abdomen by the belt 117 or a patch. Accordingly, bladder pressure can be accurately measured for a specific period of time without considerably limiting the activity of the user.

Therefore, whether bladder function is abnormal can be accurately determined.

Meanwhile, FIG. 5 is a perspective view illustrating the configuration of a bladder pressure measurement device 100a according to another embodiment of the present invention.

The above-described bladder pressure measurement device 100 is configured such that the penetrating needle 140 is first inserted into the guide tube 130 and forms an insertion hole (not shown) and then the measurement rod 120 is inserted into the guide tube 130 after the separation of the penetrating needle 140. In contrast, a bladder pressure measurement device 100a according to another embodiment of the present invention is configured such that the measurement rod 120 is inserted into a guide needle 150 that functions as both a penetrating needle and a guide tube.

The guide needle 150 includes a guide needle body 151 formed of a metal material, and a discharge slit 155 formed on the side in the axial direction of the guide needle body 151 to have a specific width.

The discharge slit 155 is formed to be larger than the diameter of the measurement rod 120 and thus allows the guide needle 150 to be easily separated from the measurement rod 120.

FIG. 6 is a view illustrating a process of using a bladder pressure measurement device 100a according to another embodiment of the present invention.

As shown in FIG. 6(a), the measurement rod 120 is first inserted into the guide needle 150. In this case, the length of the guide needle 150 is longer than that of the measurement rod 120. The lower end 153 of the guide needle 150 is formed in a sharp needle shape.

A user presses the guide needle 150 having the measurement rod 120 received therein against the abdomen of the user, thereby forming an insertion hole (not shown) in the abdomen. At the same time, the measurement rod 120 is inserted into the insertion hole (not shown). After the lower end of the measurement rod 120 has been inserted into the abdomen to a specific depth, the guide needle 150 is separated and discharged from the measurement rod 120 as shown in FIG. 6(b).

A user presses the guide needle 150 with the side of the measurement rod 120 and thus allows the discharge slit 155 of the guide needle 150 to be separated from the measurement rod 120.

Accordingly, in the state in which only the measurement rod 120 has been inserted into the abdomen, it is connected to the body unit 110 and measures bladder pressure and abdominal pressure.

Meanwhile, in the above-described bladder pressure measurement device according to the present invention, the guide tube and the measurement rod are used together, or the guide tube, the penetrating needle and the measurement rod are used together. However, in some cases, only the measurement rod may be implemented. In this case, the measurement rod may be formed of a metal material in order to facilitate the penetration thereof into the abdomen.

As described above, the bladder pressure measurement device according to the present invention can measure bladder pressure together with abdominal pressure and sphincter electromyographic activity in the state in which the measurement rod has been inserted into the abdomen of the user, and thus can accurately calculate actual detrusor pressure, exclusive of abdominal pressure.

Furthermore, an insertion hole can be easily formed in the abdomen by using the guide tube and the penetrating needle, and then the measurement rod can be inserted therein. Furthermore, the body unit is securely fastened to the abdomen of the user by a belt or a patch. Moreover, a user can measure bladder pressure in a convenient and accurate manner.

The above-described embodiments of the bladder pressure measurement device according to the present invention are illustrative only, and any person having ordinary knowledge in the art to the present invention pertains will appreciate that various modifications and other equivalent embodiments are possible. Accordingly, it can be easily understood that the scope of the present invention is not limited only to the embodiments set forth in the detailed description above. Therefore, the true technical range of protection of the present invention should be determined by the technical spirit of the attached claims. In addition, it should be understood that the scope of the present invention include all modifications, equivalents and replacements that fall within the spirit and scope of the invention that are defined by the attached claims.

The invention claimed is:

1. A device for measuring bladder pressure, comprising:
 a measurement rod configured to be inserted into an abdomen of a user, to measure both abdominal pressure and bladder pressure; and a body unit configured to be worn on a waist of the user, and be electrically connected with the measurement rod, to calculate and store detrusor pressure obtained by subtracting the measured abdominal pressure from the bladder pressure measured by the measurement rod,
wherein the measurement rod comprises:
a rod body having a predetermined length;
a bladder pressure measurement unit configured to be provided at a distal end of the rod body, to measure the bladder pressure of the user; and
an abdominal pressure measurement unit configured to be spaced apart from the bladder pressure measurement unit, to measure the abdominal pressure of the user,
wherein the abdominal pressure measurement unit comprises a plurality of abdominal pressure measurement units spaced apart from each other.

2. The device of claim 1, further comprising a guide tube configured to penetrate and be inserted into the abdomen of the user, and receive the measurement rod within it, to guide the measurement rod.

3. The device of claim 2, wherein the body unit comprises:
a body having a display unit and an input unit;
an adapter provided on the backside of the body to come into contact with the abdomen of the user, to be electrically connected with the measurement rod; and
a belt coupled to both sides of the body, and configured to be worn on the waist of the user.

4. The device of claim 3, further comprising a wireless control unit configured to be separate from the body unit, to enable an inputting person to input signals using buttons.

5. The device of claim 3, wherein the measurement rod further comprises:
a connector configured to be provided at a proximal end of the rod unit, and to be connected to the adapter.

6. The device of claim 3, further comprising a length control bracket configured to be screw-coupled with the backside of the body, to control depth of insertion of the measurement rod;
wherein the position within the abdomen, into which the abdominal pressure measurement unit is inserted, is controlled by controlling the screw coupling length between the length control bracket and the body.

7. The device of claim 2, wherein a measurement unit exposing hole having a predetermined size is formed penetrating through the outer circumferential surface of the guide tube at a position corresponding to the position of the abdominal pressure measurement unit.

8. The device of claim 2, wherein the guide tube is configured such that a sharp needle is formed at the distal end of the guide tube and a discharge slit from which the measurement rod can be separated is formed along the axial direction of the guide tube to have a diameter larger than that of the measurement rod.

9. The device of claim 2, wherein the guide tube is formed of a polymer material or a metal material.

10. The device of claim 2, wherein the guide tube is formed of a biodegradable polymer material that is degraded by body fluids.

11. The device of claim 2, further comprising a penetrating needle configured to be inserted into the guide tube, penetrate the abdomen of the user through guidance of the guide tube and then form an insertion hole through which the measurement rod is inserted polymer material.

12. The device of claim 11, wherein the penetrating needle is separated from the guide tube after its penetration into the abdomen of the user, and then the measurement rod is inserted into the abdomen through the guide tube.

13. The device of claim 1, wherein the device further comprises a sphincter electromyography unit configured to be attached to a sphincter side of the user, to measure sphincter electromyographic activity; wherein the body unit determines the normality of the organic motion of detrusor and sphincter muscles based on the measured sphincter electromyographic activity.

14. The device of claim 8, wherein the guide tube is formed of a metal material.

15. The device of claim 11, wherein the guide tube is formed of a biodegradable material.

* * * * *